United States Patent
Surina

(10) Patent No.: US 7,344,508 B2
(45) Date of Patent: Mar. 18, 2008

(54) METHOD FOR ADJUSTING METABOLIC RELATED PARAMETERS ACCORDING TO A SUBJECT'S BODY WEIGHT

(76) Inventor: Blake J Surina, 1021 Alameda Ave., Fircrest, WA (US) 98466

( * ) Notice: Subject to any disclaimer, the term of this patent is extended or adjusted under 35 U.S.C. 154(b) by 349 days.

(21) Appl. No.: 10/978,026

(22) Filed: Oct. 29, 2004

(65) Prior Publication Data

US 2006/0090765 A1 May 4, 2006

(51) Int. Cl.
*A61B 5/103* (2006.01)

(52) U.S. Cl. ..................... 600/587
(58) Field of Classification Search .......... 600/587
See application file for complete search history.

(56) References Cited

U.S. PATENT DOCUMENTS

| | | | |
|---|---|---|---|
| 4,566,461 A | 1/1986 | Lubell et al. |
| 5,387,164 A | 2/1995 | Brown, Jr. |
| 6,013,009 A | 1/2000 | Karkanen |
| 6,030,342 A | 2/2000 | Amano et al. |
| 6,138,079 A | 10/2000 | Putnam |
| 6,241,684 B1 | 6/2001 | Amano et al. |
| 6,287,262 B1 | 9/2001 | Amano et al. |
| 6,475,158 B1 | 11/2002 | Orr et al. |
| 6,554,776 B1 | 4/2003 | Snow et al. |
| 6,675,041 B2 | 1/2004 | Dickinson |

OTHER PUBLICATIONS

Astrand P.O., and D. Rodahl, *Textbook of Work Physiology: Physiological Bases of Exercise*, McGraw Hill, 1977, pp. 376-377.

*Primary Examiner*—Max F. Hindenburg
*Assistant Examiner*—Sharick Naqi
(74) *Attorney, Agent, or Firm*—Christensen O'Connor Johnson Kindness PLLC

(57) ABSTRACT

A method is provided for correcting reference parameters based on weight variations of a subject. The parameters that can be corrected may be metabolic rate, metabolic equivalent (MET), dehydration rate, drug dosage, exercise intensity, calorie usage, work level, and oxygen consumption. A corrected parameter for a subject can be determined by the factor $$P_r \frac{(wt_s)^x}{y}$$

to obtain a corrected parameter ($P_s$). In the factor, $wt_s$ is the weight of the subject, x is preferably $\frac{1}{3}$, $P_r$ is the reference parameter to be corrected, and y is preferably $(wt_r)^z$, wherein $wt_r$ is the reference weight and z is preferably $\frac{1}{3}$.

6 Claims, 3 Drawing Sheets

US 7,344,508 B2

METHOD FOR ADJUSTING METABOLIC RELATED PARAMETERS ACCORDING TO A SUBJECT'S BODY WEIGHT

FIELD OF THE INVENTION

This invention relates to adjusting metabolic related parameters such as metabolic rate, metabolic equivalent (MET), dehydration rate, drug dosages, exercise intensity, calorie usage, work level, oxygen consumption, etc., according to a subject's body weight.

BACKGROUND OF THE INVENTION

In the field of physiology, for certain exercise activities certain parameters (e.g. oxygen consumption) may be measured to provide an indication of how hard a person is working. For example, by determining a maximal oxygen consumption level that a person is able to do, and then measuring a person's actual oxygen consumption level, an indication can be given of what percentage of a person's maximum possible level they are currently working at. Certain tests (e.g. firefighter exams) may also measure selected parameters to determine an individual's performance level, and certain minimum performance levels may be required in order for an individual to pass the test. Such minimum required levels may be adjusted for different individuals (e.g. larger individuals are expected to be able to do more work).

One conventional method for expressing maximal oxygen uptake between different people is (mL oxygen consumed)/(kg body weight) wherein a 1:1 ratio between oxygen consumption and body weight is assumed to exist. In other words, as body weight increases, the maximal oxygen uptake is assumed to increase at an equal proportion. While this formula is relatively simple and easy to calculate, there are some indications that it may unfairly expect larger people to be able to do proportionally more work than they are able. At least one other known formula utilizes a more complex calculation to determine an estimate of maximal oxygen uptake. This more complex formula is (mL oxygen)/min/kg$^{2/3}$, which is disclosed by Astrand P. O. and Rodahl D. in *Textbook of Work Physiology: Physiological Bases of Exercise*, McGraw-Hill, 1977, for calculating maximal oxygen consumption. This formula seeks to account for the decreasing rate of rise in oxygen consumption as body mass increases.

The present invention is directed to an improved method that allows selected parameters to be adjusted in a simple and accurate way which takes into account the body weight of a subject.

SUMMARY OF THE INVENTION

The present invention provides a method for accurately correcting a reference metabolic parameter to obtain a predicted or corrected parameter for a given subject, or vice versa. First, one of a subject parameter ($P_s$) or a reference parameter ($P_r$) is selected for correction. The selected parameter is then adjusted in accordance with the formula $$\frac{P_s}{P_r} = \frac{(wt_s)^x}{y}$$

wherein $wt_s$ is the weight of the subject corresponding to $P_s$ and x ranges from 0.25 to 0.37, and $y=(wt_r)^z$, wherein $wt_r$ is the weight of the reference person corresponding to $P_r$ and z ranges from 0.25 to 0.37. Preferably both x and z are chosen to be the same, and more preferably to be ⅓.

In accordance with one aspect of the invention, the initial parameter may be a metabolism dependent parameter which is selected from a group consisting of metabolic rate, metabolic equivalent (MET), dehydration rate, drug dosage, exercise intensity, calorie usage, and work level. The initial parameter may also represent oxygen consumption.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
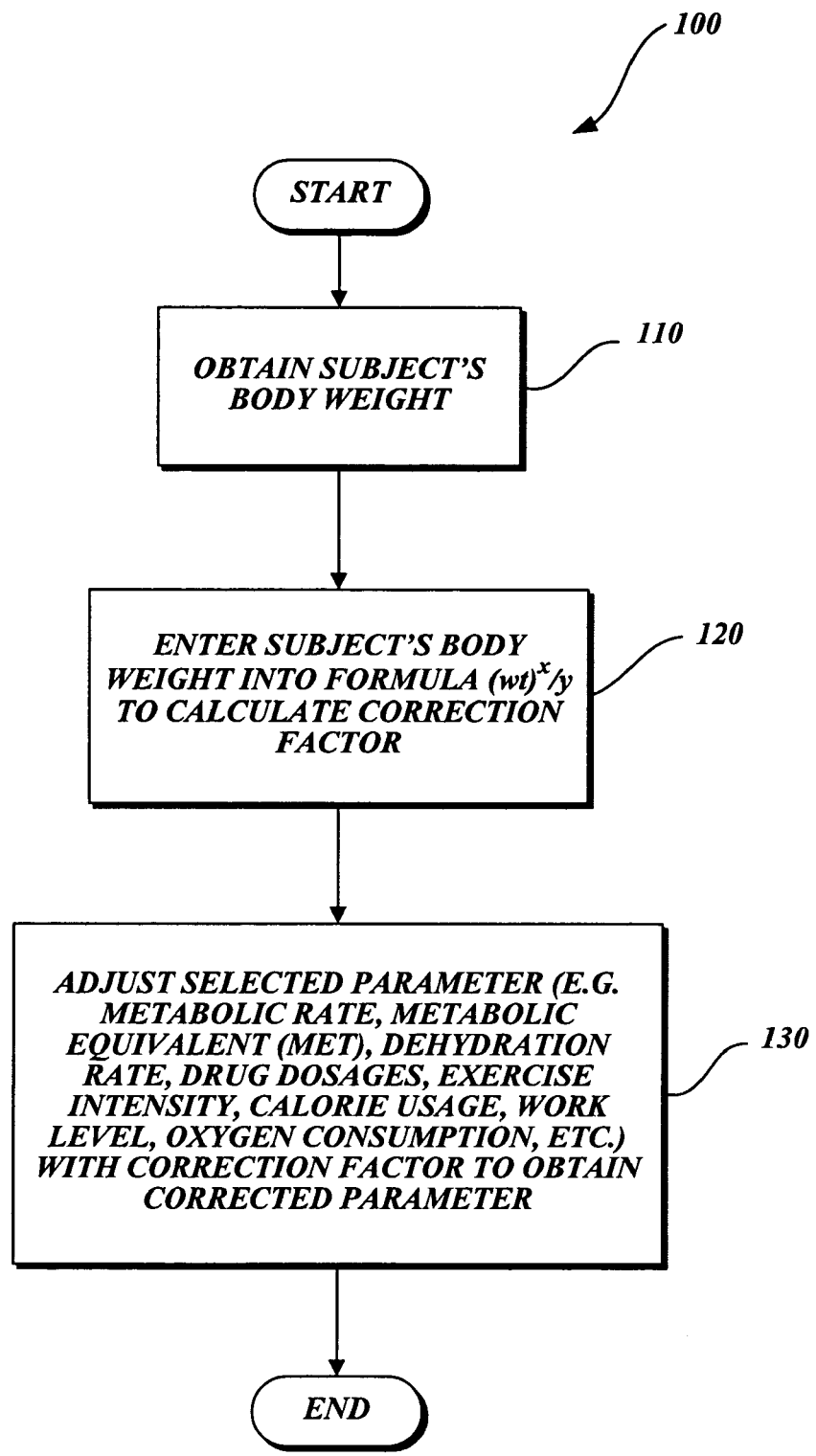
FIG. 1 is a flow diagram illustrating use of one embodiment of the equation in determining a corrected parameter.

FIG. 1 is a flow diagram of a routine 100 illustrating use of an equation for finding a corrected parameter. At a block 110, a subject's body weight ($wt_s$) is obtained. At a block 120, the subject's body weight is entered into a formula $$\frac{P_s}{P_r} = \frac{(wt_s)^x}{y} \qquad (1)$$

to calculate a correction factor. In the formula $P_s$ is the subject parameter, $P_r$ is the reference parameter and y is the reference correction factors based on the reference body weight ($wt_r$) taken from a reference study or chart. The exponent x may range from 0.25 to 0.37. The factor y is calculated by the formula $y=(wt_r)^z$ where z ranges from 0.25 to 0.37. Preferably x and z are the same, and more preferably ⅓. At a block 130, the reference parameter ($P_r$) (e.g. metabolic rate, metabolic equivalent (MET), dehydration rate, drug dosages, exercise intensity, calorie usage, work level, oxygen consumption, etc.) is adjusted with the correction factor to obtain a corrected parameter for the subject $P_s$ by the formula $$P_s = P_r \frac{(wt_s)^x}{y} \qquad (2)$$

The parameters that can be adjusted with the formula $(wt)^x/y$ are those parameters related to metabolic function of a reference individual having a reference body weight. For example, the parameter may be oxygen consumption or related to oxygen consumption (e.g. metabolic dependent parameters such as metabolic rate, metabolic equivalent (MET), dehydration rate, drug dosages, exercise intensity, calorie usage, work level, etc.). An individual's level of oxygen consumption is influenced by body mass, specifically, muscle mass, lung capacity, blood volume and similar factors. The formula $(wt)^x/y$ allows for the adjustment of parameters for a subject individual which accounts for variation in body mass between the subject individual and a reference individual. The factor can be used to find the estimated level of metabolic related function of a subject individual based on a previously measured parameter of a reference individual having a reference body weight. The factor that is produced by the formula can also be used to convert a subject's measured parameters to the equivalent level for a reference individual.

To use the correction factor to predict a subject's metabolic parameter from a reference study, the subject's body weight in kilograms is entered into the formula. The denominator y is determined by the reference weight ($wt_r$) found in the reference study. A typical reference body weight is 75 kg. For a reference weight of 75 kg, y is 4.22. y can be varied from 3.0 to 5.8 representing reference body weights from 27 kg to 195 kg. The value of y of course is dependent upon the reference weight, and more preferably from 3.4 to 4.8, without significantly altering the adjustment using the correction factor.

For example, for a reference weight of 75 kg (which yields a y=4.22), a test subject weight of 125 kg provides a correction factor ($wt_s^x/y$) equal to 1.18. If the reference individual (with a reference weight of 75 kg) can do 2 units of work, this reference work parameter $P_r$ is then multiplied by the correction factor 1.18 in accordance with equation (2) to indicate that the 125 kg test subject is expected to be able to do an estimated equivalent of 2.36 units of work.

Alternatively, if a subject has actually been measured for a metabolic parameter, that parameter can be corrected to compare with a reference study by the formula $$P_r = P_s \frac{y}{(wt_s)^x} \quad (3)$$

In this example, the measured parameter ($P_s$), the correction factor y based on the reference weight for the study to be compared, and the subject's weight are entered in the formula. Assuming the subject is measured to perform 2.36 units of work, the subject's weight is 125 kg, and the reference weight is 75 kg, then the predicted reference parameter $P_r$ can be calculated as 2.0. This predicted reference value can then be compared to the actual reference value.

Figure 2:
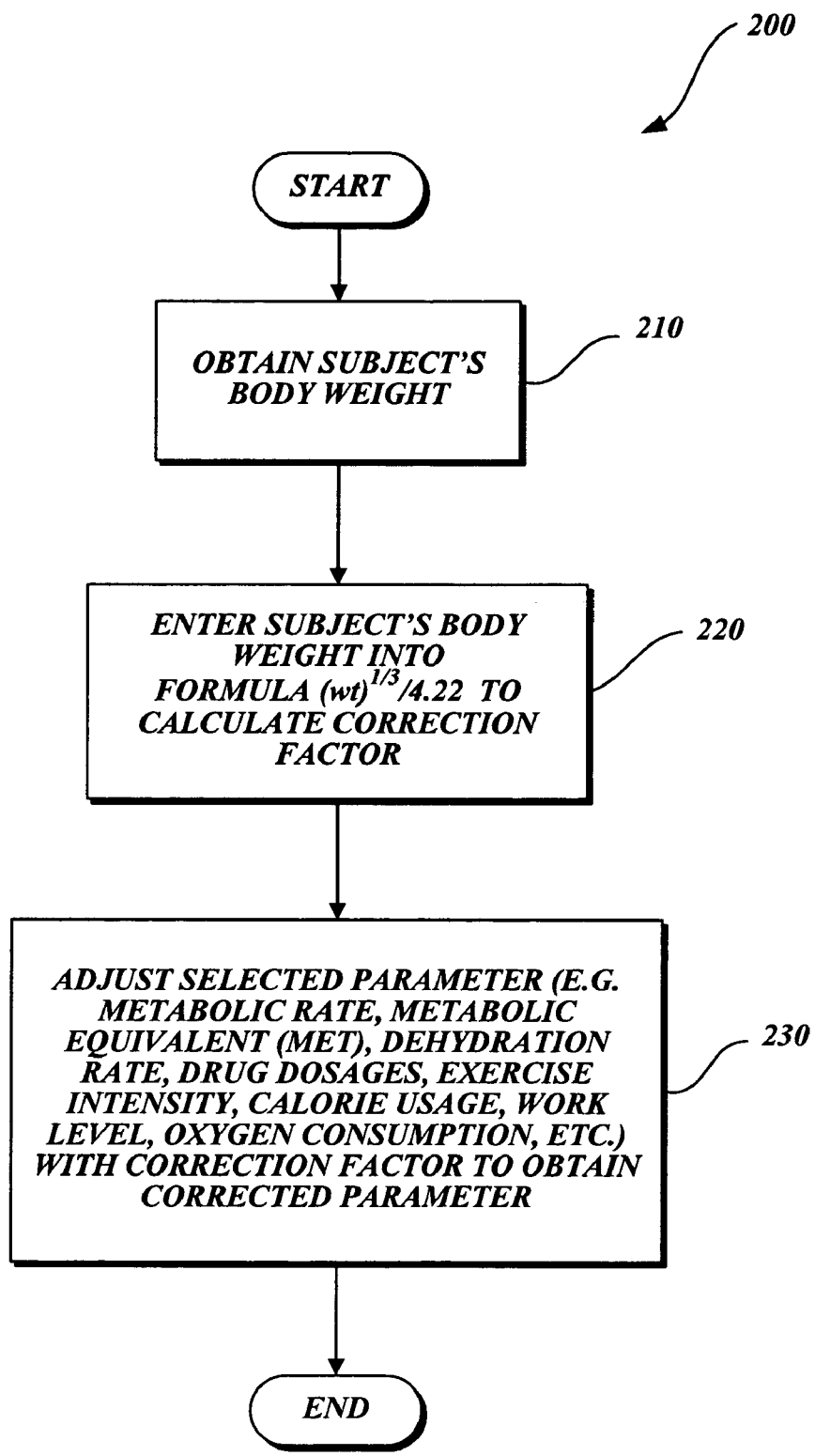
FIG. 2 is a flow diagram illustrating use of a second embodiment of the equation in determining a corrected parameter.

FIG. 2 is a flow diagram of a routine 200 illustrating use of an equation for finding a corrected parameter. At a block 210, a subject's body weight is obtained. At a block 220, the subject's body weight is entered into a formula $(wt)^x/y$ to calculate a correction factor. At a block 230, a reference parameter (e.g. metabolic rate, metabolic equivalent (MET), dehydration rate, drug dosages, exercise intensity, calorie usage, work level, oxygen consumption, etc.) is selected from a reference chart or study. The reference weight for the study is determined and entered into the correction factor to obtain a corrected parameter. One of ordinary skill will readily recognize that this calculation can readily be implemented by computer.

Figure 3:
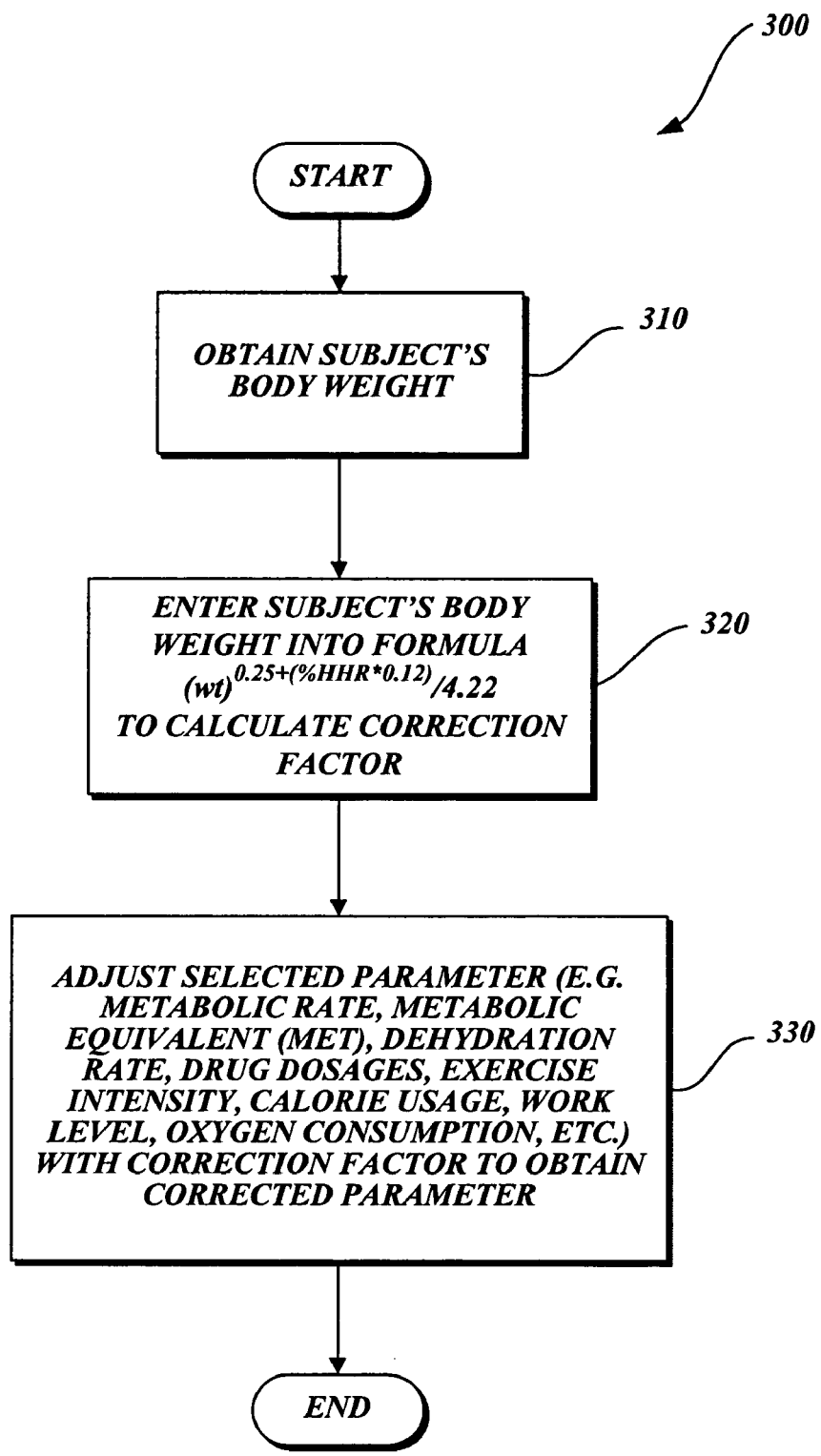
FIG. 3 is a flow diagram illustrating use of a third embodiment of the equation in determining a corrected parameter.

FIG. 3 is a diagram of a routine 300 illustrating use of an equation for finding a corrected parameter that includes a factor which accounts for work intensity as measured by heart rate reserve. This correction factor is used for resting heart rate corrections. Heart rate reserve is a standardized measure of heart rate expressed as a percentage of the difference between resting heart rate and maximum heart rate. At a block 310, a subject's body weight is obtained. At a block 320, the subject's body weight is entered into a formula $$(wt_s)^{0.25+(\%HRR*0.12)}/y \quad (4)$$

wherein % HHR is heart rate reserve as a percentage of the difference between resting and maximum heart rate, to calculate a correction factor. In this formula, heart rate reserve is multiplied by a factor of 0.12, which represents the variation in the slopes of body weight plotted against oxygen consumption for resting versus maximal work states. The formula (4) is then substituted for the factor $(wt_s)^x/y$ in the right side of formula (1). At a block 330, a selected parameter ($P_r$) (e.g. metabolic rate, metabolic equivalent (MET), dehydration rate, drug dosages, exercise intensity, calorie usage, work level, oxygen consumption, etc.) is adjusted by the correction factor (3) to obtain a corrected parameter.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for correcting a parameter for weight variation comprising the steps of:
    selecting one of a subject person parameter ($P_s$) and a reference person parameter ($P_r$),
    adjusting the other parameter in accordance with the formula $$\frac{P_s}{P_r} = \frac{(wt_s)^x}{y} \quad (1)$$

wherein $wt_s$ is the weight of the subject person corresponding to $P_s$ and x ranges from 0.25 to 037, and wherein $y=(wt_r)^z$, wherein $wt_r$ is the weight of the reference person corresponding to $P_r$ and z ranges from 0.25 to 0.37 to provide an adjusted parameter, and
    presenting the adjusted parameter for comparison with a measured or preselected parameter for the subject person.

2. The method of claim 1, wherein y is in the range of 3.0 to 5.8.

3. The method of claim 1, wherein $$\frac{(wt_s)^x}{y} \text{ is } \frac{(wt_s)^{0.25+(\%HRR*0.12)}}{y},$$

wherein % HRLR is the heart rate reserve as a percent of maximum heart rate for the subject.

4. The method of claim 1, wherein the selected parameter is a metabolism dependent parameter which is selected from the group consisting of metabolic rate, metabolic equivalent (MET), dehydration rate, drug dosage, exercise intensity, calorie usage, and work level.

5. The method of claim 1, wherein the selected parameter is oxygen consumption.

6. The method of claim 1, wherein the $$\frac{(wt_s)^x}{y} \text{ is } \frac{(wt_s)^{1/3}}{4.22}.$$

* * * * *

UNITED STATES PATENT AND TRADEMARK OFFICE
CERTIFICATE OF CORRECTION

PATENT NO. : 7,344,508 B2
APPLICATION NO. : 10/978026
DATED : March 18, 2008
INVENTOR(S) : B. J. Surina It is certified that error appears in the above-identified patent and that said Letters Patent is hereby corrected as shown below:

| COLUMN | LINE | ERROR |
|--------|------|-------|
| 4 | 33 | "037," should read --0.37,-- |

Signed and Sealed this

Fourth Day of November, 2008

JON W. DUDAS
*Director of the United States Patent and Trademark Office*